United States Patent [19]

Louit

[11] 4,099,407
[45] Jul. 11, 1978

[54] METHOD FOR MEASURING THE PRE-STRESS IN HOOP-BOUND ANULUSES OF RECTANGULAR CROSS-SECTION AND MADE OF PIEZOELECTRIC CERAMIC MATERIAL

[75] Inventor: Henri Louit, Toulon, France

[73] Assignee: Compagnie Industrielle des Telecommunications Cit-Alcatel S.A., Paris, France

[21] Appl. No.: 798,720

[22] Filed: May 19, 1977

[30] Foreign Application Priority Data

Jun. 9, 1976 [FR] France .................................. 76 17453

[51] Int. Cl.² ........................ G01N 3/36; G01R 29/22; G01N 33/38
[52] U.S. Cl. .................................... 73/88.5 R; 324/56
[58] Field of Search ........... 73/88 R, 88.5 R, DIG. 4; 324/56

[56] References Cited

U.S. PATENT DOCUMENTS

| | | | |
|---|---|---|---|
| 2,802,984 | 8/1957 | Sussman | 324/56 |
| 3,561,831 | 2/1971 | Alibert et al. | 73/DIG. 4 |
| 3,742,757 | 7/1973 | Callahan | 73/88.5 R |

Primary Examiner—James J. Gill
Attorney, Agent, or Firm—Sughrue, Rothwell, Mion, Zinn and Macpeak

[57] ABSTRACT

A static stress and a sinusoidal dynamic stress are applied to the internal surface of the anulus. The electric voltage between the internal surface and the external surface of the anulus is measured for each value of the static stress. The static stress at which the sinusoidal voltage is maximum corresponds to the pre-stress due to the binding.

1 Claim, 2 Drawing Figures

METHOD FOR MEASURING THE PRE-STRESS IN HOOP-BOUND ANULUSES OF RECTANGULAR CROSS-SECTION AND MADE OF PIEZOELECTRIC CERAMIC MATERIAL

FIELD OF THE INVENTION

The present invention relates to a method and a device for measuring the pre-stress in hoop-bound annuluses having a rectangular cross-section and made of piezoelectric ceramic material.

BACKGROUND OF THE INVENTION

It is known to bind annuluses made of piezoelectric ceramic material to reduce their fragility and thus to allow their fatigue ratio and their permissible power to be increased.

It is necessary to measure the stress which has been induced by binding to ensure that it corresponds to the required stress.

SUMMARY OF THE INVENTION

The method of measuring the pre-stress in hoop-bound annuluses having a rectangular cross-section, made of piezoelectric ceramic material according to the invention comprises the steps of:

Imposing a main stress on the internal cylindrical surface of a ceramic annulus which can assume several values and a subdidiary stress which varies sinusoidally;

Measuring the coefficient of deformation $d$ or the coefficient of stress $g$ of the ceramic annulus for each value of the main stress;

Noting the applied main stress whih corresponds to the maximum of the coefficient measured this applied main stress being equal in absolute value to the pre-stress due to binding.

The method according to the invention is based on the fact that the piezoelectric deformation coefficient $d$ or stress coefficient $g$ decreases appreciably when the ceramic substance is subjected to a static stress in compression or tension. These coefficients therefore go through a maximum at zero stress.

The device according to the invention allowing said method to be brought into effect comprises a sealed chamber filled with liquid whose lateral surface is cylindrical and is constituted by a resilient wall round which said ceramic annulus is fitted, said resilient wall then being pressed against the internal cylindrical surface of the annulus.

Means are provided for supplying a determined main pressure P in said chamber and to make said pressure vary.

Means are further provided for reading said mean pressure and means are provided for applying a subsidiary pressure in said chamber which varies sinusoidally and has a determined maximum amplitude.

Means are provided also for measuring the sinusoidal electric voltage between the cylindrical internal surface and the cylindrical external surface of the ceramic annulus. The maximum voltage is obtained for a main pressure P which imposes a stress of the same absolute value as the pre-stress due to the binding.

BRIEF DESCRIPTION OF THE DRAWINGS

The present invention will be better understood from the following description.

DESCRIPTION OF THE PREFERRED EMBODIMENT

Figure 1:
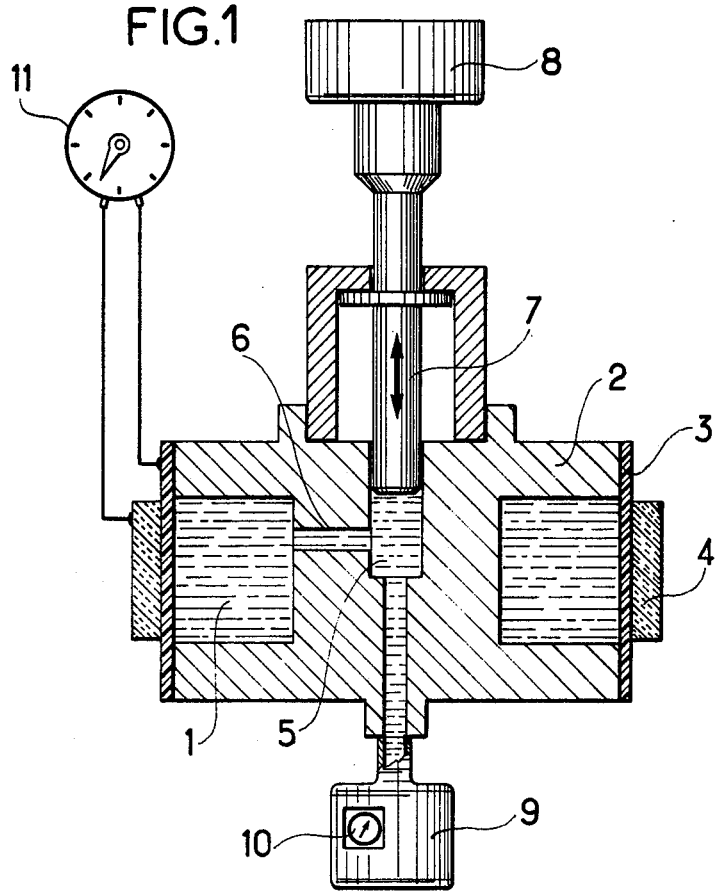
FIG. 1 is a sectional view of a device embodying the invention.

FIG. 1 shows a measuring device embodying the invention which comprises a sealed toroidal chamber 1 with a vertical axis, formed in a block 2. The cylindrical external wall of this chamber 1 is formed by a resilient wall 3. The outside diameter of the chamber 1 is equal to the inside diameter of the toroidal rings such as ring 4 to be pre-stressed. These rings 4 have a rectangular cross-section and their height is equal to the height of the chamber 1. The central part of the block 2 comprises a tube 5 with a vertical axis connected by a pipe 6 to the chamber 1.

This tube 5 is blocked at is upper part by the piston 7 of an exciter 8. The piston can slide vertically inside the tube 5.

The lower part of the tube 5 is connected to a hydraulic pump 9 fitted with a gauge 10.

The chamber 1 as well as the tube 5 are filled with liquid.

The terminals of a volmeter 11 are connected to the cylindrical internal and external surfaces of the ring 4.

A main pressure P is applied by the pump 9. This pressure is measured by the gauge 10 and knowing the cylindrical external surface area S of the chamber 1, the stress $T = P/S$ applied to the resilient wall 3 is deduced directly.

By means of the exciter 8, a subsidiary pressure which varies simusoidally is applied to the liquid contained in the tube 5, the maximum amplitude of this pressure being $p$.

It is known that the stress coefficient $g$ is given by the following formula:

$$g = V/pe$$

$e$ being the thickness of the ceramic ring, $p$ being the maximum amplitude of the sinusoidal subsidiary pressure, and V being the sinusoidal difference in potential between the internal cylindrical surface and the external cylindrical surface of the ring 4 measured by the voltmeter 11.

Now, it is also known that $g$ is a function of the stress T.

This function is at its maximum when T is equal in absolute value and of opposite sign to C, the pre-stress due to the binding, since for this value of T, the ceramic substance is no longer subject to any static stress either in tension or in compression.

Figure 2:
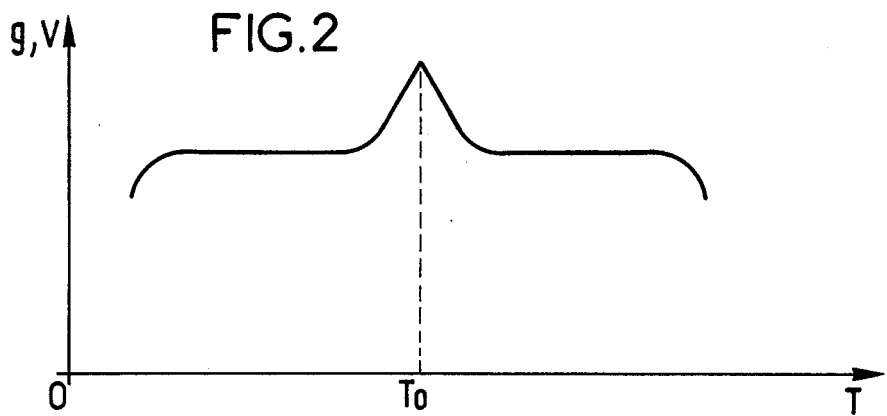
FIG. 2 is a plot of the variation of the piezoelectric coefficients of the annulus made of a hoop-bound ceramic substance as a function of the stress applied to the internal surface of the annulus.

For each value of T which is deduced from the value of the pressure P read on the gauge 10, a value of V is read on the voltmeter 11 which gives a value proportional to $g$. The curve in FIG. 2 is obtained by plotting along the y axis values of $g$ or of a proportional magnitude, for example V or $d$ (coefficient of deformation $d = \epsilon g$), against values of T plotted along the X axis.

This curve presents a maximum for a degree of stress To this allowing the pre-stress C due to the binding to be deduced since C is equal to To in absolute value.

What I claim is:

1. A method for measuring the pre-stress in a hoop-bound annulus having a rectangular cross-section and made of piezoelectric ceramic material, said method comprising the steps of:

applying a pressure stress on the internal cylindrical surface of said annulus, said pressure stress having a main continuous component and a subsidiary sine-shaped component, varying the main continuous component while keeping the maximum amplitude of said subsidiary sine-shaped component at a constant value, said main continuous component assuming several values, and measuring the sinusoidal electric voltage generated across the annulus by the subsidiary component of said pressure stress for each value of the main continuous component, whereby, the main continuous pressure stress component which corresponds to the maximum value of said voltage is a measure equal, in absolute value, of the pre-stress due to binding.

* * * * *